United States Patent [19]
Hamilton

[11] Patent Number: 5,977,439
[45] Date of Patent: *Nov. 2, 1999

[54] BINARY BAC VECTOR

[75] Inventor: Carol Marie Hamilton, Ithaca, N.Y.

[73] Assignee: Cornell Research Foundation, Inc., Ithaca, N.Y.

[ * ] Notice: This patent is subject to a terminal disclaimer.

[21] Appl. No.: 08/996,382

[22] Filed: Dec. 22, 1997

Related U.S. Application Data

[63] Continuation of application No. 08/372,605, Jan. 13, 1995, Pat. No. 5,733,744.

[51] Int. Cl.[6] .......................... C12N 15/84; C12N 15/70; A01H 5/00; A01H 5/10
[52] U.S. Cl. ......................... 800/294; 800/298; 800/300; 435/252.33; 435/320.1; 435/418; 435/419; 435/469; 435/488
[58] Field of Search ................................ 435/172.3, 419, 435/320.1, 469, 418, 488, 252.33; 800/205, 298, 294, 300

[56] References Cited

U.S. PATENT DOCUMENTS

| | | | |
|---|---|---|---|
| 4,693,976 | 9/1987 | Schilperoort et al. | 435/172.3 |
| 4,880,741 | 11/1989 | Davidow et al. | 435/172.3 |
| 4,889,806 | 12/1989 | Olson et al. | 435/172.3 |
| 4,940,838 | 7/1990 | Schilperoort et al. | 800/205 |
| 5,068,193 | 11/1991 | Comai | 435/252.3 |
| 5,098,838 | 3/1992 | Goodman et al. | 435/183 |
| 5,149,645 | 9/1992 | Hoekema et al. | 435/172.3 |
| 5,187,073 | 2/1993 | Goldman et al. | 435/172.3 |
| 5,262,306 | 11/1993 | Robeson et al. | 435/29 |
| 5,270,201 | 12/1993 | Richards et al. | 435/240.4 |
| 5,275,942 | 1/1994 | Vos | 435/172.3 |
| 5,286,635 | 2/1994 | Hanson et al. | 435/172.3 |

OTHER PUBLICATIONS

J.C. Pierce et al., "A Positive Selection Vector for Cloning High Molecular Weight DNA by the Bacteriophage P1 System: Improved Cloning Efficacy," *Proc. Natl. Acad. Sci. USA*, 89:2056–2060 (Mar. 1992).

L. Jouanin et al., Localization and Restriction Maps of the Replication Origin Regions of the Plasmids of *Agrobacterium rhizogenes* Strain $A_4$ *Mol Gen Genet* 201:370–374 (1985).

Ma, H. et al., "Vectors for Plant Transformation and Cosmid Libraries," *Gene* 117:161–167 (1992).

McBride et al., "Improved Binary Vectors for Agrobacterium–Mediated Plant Transformation," *Plant Molecular Biology*, 14:269–276 (1990).

Shizuya et al., "Cloning and Stable Maintenance of 300–Kilobase–Pair Fragments of Human DNA in *Escherichia Coli* Using an F–factor–based Vector," *PNAS USA*, 889:8794–8797 (1992).

Bevan, "Binary Agrobacterium Vectors for Plant Transformation," *Nucleic Acids Research*, 12(22):8711–8721 (1984).

Bhattacharyya et al., "Reduced Variation in Transgene Expression from a Binary Vector with Selectable Markers at the Right and Left T–DNA Borders," *The Plant Journal*, 6(6):957–968 (1994).

Hamilton, "A Binary–BAC System for Plant Transformation with High–Molecular–Weight DNA," *Gene*, 200:107–116 (1997).

Hajdukiewicz et al., "The Small, Versatile pPZP Family of Agrobacterium Binary Vectors for Plant Transformation," *Plant Molecular Biology*, 25:989–994 (1994).

*Primary Examiner*—David T. Fox
*Attorney, Agent, or Firm*—Nixon Peabody LLP

[57] ABSTRACT

The present invention is directed to a vector for transferring heterologous DNA into a plant cell. The vector is based on the bacterial artificial chromosome (BAC) vector designed for the construction of genomic libraries with large DNA inserts, and the binary (BIN) vector designed for Agrobacterium-mediated plant transformation. The BIBAC vector according to the subject invention allows the construction of plant genomic libraries with large DNA inserts that can be directly introduced into plants by transformation mediated by Agrobacterium.

18 Claims, 2 Drawing Sheets

BINARY BAC VECTOR

CROSS-REFERENCE TO RELATED APPLICATIONS

This application is a continuation of application Ser. No. 08/372,605 filed Jan. 13, 1995, now U.S. Pat. No. 5,733,744.

The subject matter of this application was made with support from the United States Government (National Science Foundation Plant Science Center Grant No. 175-8300-6550-361).

FIELD OF THE INVENTION

The present invention relates to a vector for plant transformation, and more particularly to a binary BAC vector and to uses of the vector.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The main problem facing plant molecular biologists and plant breeders today is how to identify agriculturally important genes that are known only by their phenotype. Although map-based cloning and transposon tagging have made it possible to identify plant genomic clones by observing a phenotype, it is a technically difficult and labor intensive process. To date only a few major plant genes of this type have been cloned (Martin et al. 1993, Bent et al. 1994, Jones et al. 1994, Whitham et al. 1994).

Plant breeders have always relied on genetic variation for classical breeding programs. To be most effective, modern plant breeders need to know the molecular biology of genes that are important to agriculture. If the gene coding for a desired trait has been cloned, it is now possible, in some instances, to bypass classical breeding techniques and to directly introduce that trait by plant transformation. In the future it may even be possible to introduce desirable traits from species that are not cross-compatible, something that cannot be achieved by classical plant breeding. The cloning of agriculturally important genes will also open up new areas of research in plant biology.

When the idea of map-based cloning was first envisioned, a chromosome walk to link up overlapping genomic clones in the region of interest was considered a necessity. Crop plants tend to have relatively large genomes and high levels of repetitive DNA, features that make chromosome walking more tedious and more complicated. Fortunately, the recent development of methods that make it possible to identify molecular markers closely linked to a gene have led to the concept of chromosome landing.

Chromosome landing is based on the fact that it is no longer that difficult to obtain markers that are closely linked to a gene of interest, even in a genome that is not well characterized. RAPD (random amplified polymorphic DNA) and AFLP (amplified fragment length polymorphism) methods in combination with analysis of near isogenic lines or bulked segregants can be used to identify molecular markers that are very close to a gene of interest (Williams et al. 1990, Zabeau and Vos 1992, Martin et al. 1991, Michelmore et al. 1991). A genomic library can then be screened using markers that flank the gene to identify potential clones. Currently, the most significant hurdle remaining for the wide scale application of map-based cloning is how to verify that a potential clone does indeed carry the gene of interest. Until now, the approach has been to generate a series of subclones of a yeast artificial chromosome (YAC) (Burke et al. 1987) or bacterial artificial chromosome (BAC) believed to contain a gene of interest. Each of these subclones must then be individually transformed into plants to identify the presence (or absence) of the gene by assaying transgenic plants for the expected phenotype. Not only is this very time consuming, it is a risky proposition since any given subclone may contain only part of the target gene, and thus give a negative result in transformation/complementation experiments. If the target gene contains a large number of introns and thus stretches over a large segment of genomic DNA, then none of the subclones will be sufficiently large to contain the entire gene.

What is needed most is technology that can circumvent this bottleneck of gene verification. The ability to transfer large DNA constructs to plants would reduce the amount of subcloning required from a high molecular weight YAC or BAC library vector before proceeding on to plant transformation. A high molecular weight library vector that can be used to transform plants directly would be ideal. Indeed, the development of technology to transform plants with high molecular weight DNA will be essential for the cloning of QTLs (quantitative trait loci) which make up the major portion of agriculturally important genes.

None of the existing vectors for high molecular weight genomic libraries are suitable for plant transformation. A series of cosmid library vectors (maximum insert size 46 kb) suitable for Agrobacterium-mediated plant transformation were constructed by Ma et al. (1992). However, the small insert size makes them less practical for genomes much larger than Arabidopsis. Whereas Arabidopsis is an attractive model system because its genomic size is small, about 100 megabase-pairs (Mbp), other higher plants have 4–20-fold larger genomes (Bennett and Smith 1976). The first high molecular weight plant genomic libraries were constructed in YAC vectors. The Pto disease resistance gene from tomato (Martin et al. 1992) and the RPS2 disease resistance gene from Arabidopsis (Bent et al. 1994) have been cloned from YAC libraries. However, a YAC library is a major investment to construct, maintain and utilize, and some YAC libraries have been plagued by deletions, rearrangements, and chimeras (Anderson 1993).

Recently, BAC libraries have been constructed for sorghum (Woo et al. 1994) and for rice (Wang and Ronald 1994) with average insert sizes of about 180 kb. BAC libraries have proven to be easier to construct, screen and maintain than YAC libraries.

*Agrobacterium tumefaciens* is a naturally occurring plant transformation system (see generally, review by Kado 1991; and Zambryski 1988). Recently, Miranda et al. showed that at least 170 kb could be transferred from the Ti plasmid of Agrobacterium to a plant genome (Miranda et al. 1992). The most dramatic potential for Agrobacterium-mediated transformation of plants with high molecular weight constructs is that A. tumefaciens has been shown to transfer its T-DNA to the plant genome in a linear fashion. It would be a tremendous advantage if transgenic plants could be generated that carry the entire genomic library insert (intact) in the plant genome. Linear transfer would eliminate the possibility of truncated genes except at the limits of the inserts, and make it possible to introduce very large plant genes (if they exist), or gene clusters.

Agrobacterium-mediated plant transformation is the most widely used technique for introducing new genetic information into plant cells. Agrobacterium-mediated transformation is routinely applicable in species like tobacco, petunia, and tomato, and a considerable amount of effort has gone into applying this technique to major crop species (reviewed by van Wordragen and Dons 1992) and monocot species. Recently, Agrobacterium-mediated transformation of rice has been reported (Hiei et al. 1994).

A need continues to exist, however, for a vector to transform plants with high molecular weight DNA sequences.

SUMMARY OF INVENTION

This need is met by the construction of a new BAC library vector that has been designed for Agrobacterium-mediated plant transformation, according to the subject invention. Since each BIBAC library clone exists as a plasmid in *Escherichia coli*, the DNA of individual clones can be readily isolated by standard plasmid isolation techniques. This plasmid DNA can then be introduced into Agrobacterium by electroporation. Alternatively, BIBAC library clones can be transferred from an *E.coli* host to Agrobacterium by tri-parental mating.

The invention provides a vector for transferring heterologous DNA into a plant cell. The vector includes a backbone having a first origin of replication capable of maintaining heterologous DNA as a single copy in an *Escherichia coli* host cell and a second origin of replication capable of maintaining heterologous DNA as a single copy in an *Agrobacterium tumefaciens* host cell. The vector further includes a unique restriction endonuclease cleavage site for insertion of heterologous DNA, and left and right Agrobacterium T-DNA border sequences flanking the unique restriction endonuclease cleavage site. The T-DNA border sequences allow introduction of heterologous DNA located between the left and right T-DNA border sequences into a plant cell.

The vector allows the construction of plant genomic libraries with large DNA inserts. Individual clones can be directly introduced into plants by transformation.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

Figure 1:
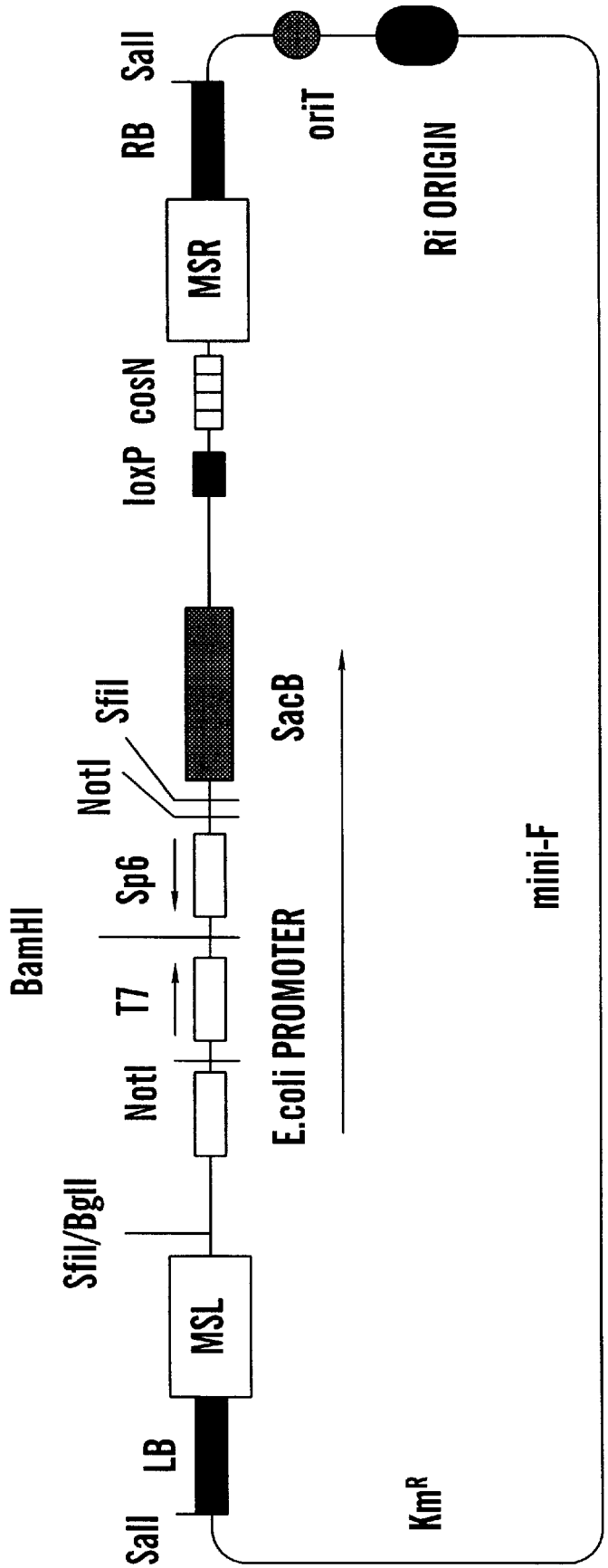
FIG. 1 shows the map of the BIBAC vector.

The vector designated BIBAC has been deposited as the plasmid designated pCH23 in the *Escherichia coli* strain designated DH10B(pCH23) pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 69743.

The present invention relates to a vector for transferring heterologous DNA into a plant cell. The vector includes a backbone having two origins of replication. The first origin of replication is capable of maintaining the heterologous DNA as a single copy in an *Escherichia coli* host cell. As used throughout this application, unless otherwise indicated, maintenance as a single copy refers to a non-replicating cell, i.e. a cell not undergoing cell division; during cell division, the copy per cell increases to nearly two complete copies per cell. The second origin of replication is capable of maintaining the heterologous DNA as a single copy in an *Agrobacterium tumefaciens* host cell.

The vector also includes a unique restriction endonuclease cleavage site for the insertion of heterologous DNA. The presence of only one cleavage site for a particular restriction endonuclease within the DNA sequence encoding the vector is the presence of a "unique" restriction endonuclease cleavage site. The particular restriction endonuclease will, therefore, only cleave the DNA at that one location or "unique site". Heterologous DNA refers to DNA not normally present in the particular host cell transformed by the vector.

The vector also includes left and right Agrobacterium T-DNA border sequences flanking the unique restriction endonuclease cleavage site (Peralta and Ream 1985). These border sequences allow the introduction of heterologous DNA located between the left and right T-DNA border sequences into a plant cell.

Stable maintenance of high molecular weight DNA in *Escherichia coli* and *Agrobacterium tumefaciens* is made possible because these high molecular weight DNA sequences are carried on a single copy plasmid. With multiple copies of such large DNA inserts, the unstable host cells would not be useful for plant transformation.

In one embodiment of the vector of the subject invention, designated the BIBAC vector, the unique restriction endonuclease cleavage site is a BamHI cleavage site. This cleavage site is located between the *Agrobacterium tumefaciens* T-DNA border sequences, as is a selection marker for incorporation of heterologous DNA into the vector (the sacB gene). The BamHI cleavage site and the sacB gene are located such that when heterologous DNA is inserted into the BamHI site the sacB gene is inactivated. The BIBAC vector includes the F origin of replication from *Escherichia coli* for maintaining the heterologous DNA as a single copy in *Escherichia coli* (Low 1972), and the Ri origin of replication from *Agrobacterium rhizogenes* for maintaining the heterologous DNA as a single copy in *Agrobacterium tumefaciens*. The left and right T-DNA border sequences in the BIBAC vector are derived from the TL-DNA of the octopine plasmid pTiA6.

The BIBAC vector also includes a selection marker for introduction of the heterologous DNA into the bacterial cells *Escherichia coli* and *Agrobacterium tumefaciens*. The bacterial selection marker comprises the kanamycin resistance gene. The BIBAC vector also includes a selection marker for introduction of the heterologous DNA into a plant cell. This selection marker must be located between the left and right T-DNA border sequences, since only the region emcompassed by the border sequences is transferred into the plant host cell. Therefore, the plant selection marker must lie between the T-DNA borders for transfer into the plant cell. In the BIBAC vector, the plant selection marker is for kanamycin resistance (provided by the GUS-NPTII construct). Other suitable plant selection markers include hygromycin resistance (the HYG construct) and phosphinothricin resistance (provided by the BAR-GUS construct).

The BIBAC vector also includes an origin of conjugal transfer (the oriT origin from plasmid RK2). This origin allows the transfer of heterologous DNA from an *Escherichia coli* host cell directly to an *Agrobacterium tumefaciens* host cell by bacterial conjugation.

The vector is used to introduce heterologous DNA into a host cell. Accordingly, the vector preferably includes heterologous DNA inserted into the unique restriction endonuclease cleavage site. DNA is inserted into the vector using standard cloning procedures readily known in the art. This generally involves the use of restriction enzymes (in the case of BIBAC, BamHI) and DNA ligases, as described by Maniatis et al., *Molecular Cloning: A Laboratory Manual*, Cold Spring Harbor Laboratory Press, Cold Spring Harbor, New York [1982]. The vector can then be used to transform a host cell, such as *Escherichia coli, Agrobacterium tumefaciens*, and/or a plant cell.

There are numerous uses of the vector according to the subject invention. One use is as a library cloning vector. Genomic DNA from a plant can be cut with a restriction endonuclease (BamHI in the case of the BIBAC vector). The restriction fragments which represent collectively the entire genome of the plant are then each ligated into a BIBAC vector (which has been opened by cutting with BamHI). This generates a library in the BIBAC vector. (See generally, *Current Protocols in Molecular Cloning*, Ausubel, F.M. et al., eds., Greene Publishing and Wiley Interscience, New York (1989).)

For ease in working with the library, the vector is generally maintained in a bacterial host cell. *Escherichia coli* is a standard bacterial host cell for maintaining such a DNA library. The vector DNA can be introduced into the bacterial host cell by various methods known in the art. These include electroporation, calcium chloride transformation, and transformation by particle bombardment. The transformed bacterial cells can be identified by their ability to grow on various selective agents. Accordingly, bacterial cells that contain the vector can be identified by their resistance to kanamycin. The presence of inserted heterologous DNA is indicated by the ability of the bacteria to grow on high levels of sucrose. The ability to grow on high levels of sucrose is due to the inactivation of another selection marker, the sacB gene. Potential clones containing the desired heterologous DNA can be identified by Southern analysis (Southern 1975) using closely linked molecular markers or heterologous DNA as probe. Clones (vector containing heterologous DNA) of interest are then used for further experiments.

The vector, or a derivative clone of interest (as described above), can be introduced into *Agrobacterium tumefaciens*. This introduction can be accomplished using methods known to those in the art, including electroporation, or particle bombardment. Another method that can be used to introduce the vector into *Agrobacterium tumefaciens* is triparental mating. In a triparental mating, the *Escherichia coli* containing the vector, a second *Escherichia coli* containing a helper plasmid, and an Agrobacterium are combined, resulting in introduction of the vector DNA into the Agrobacterium. The Agrobacterium cells are then screened using a selection marker (such as kanamycin resistance in the BIBAC vector), for the presence of the vector DNA therein. Those cells containing the vector DNA are then used for further experiments.

The vector, or a derivative clone of interest (as described above), can also be introduced into a plant cell. (See generally, *Plant Molecular Biology Manual*, 2nd Edition, Gelvin, S. B. and Schilperoort, R. A., Eds., Kluwer Academic Press, Dordrecht, Netherlands (1994).)

One method for introduction of the vector or clone into a plant cell is Agrobacterium-mediated transformation of the plant cell (stable or transient). Briefly, the tissue of plants is contacted with an inoculum of the Agrobacterium transformed with the vector (with heterologous DNA therein). Generally, this procedure involves inoculating the plant tissue with a suspension of the bacteria and incubating the tissue for 48 to 72 hours on regeneration medium without antibiotics at 25–28° C.

In practice, the method of Agrobacterium-mediated transformation can involve a three-step process. The vector DNA is first analyzed in an *Escherichia coli* host cell, and is then introduced into an *Agrobacterium tumefaciens* host cell, which is then used for Agrobacterium-mediated transfer of the T-DNA within the vector to the plant cell. Generally, only a portion of the T-DNA border sequences and DNA located therebetween is transferred into the plant cell by such Agrobacterium-mediated transfer. Therefore, any heterologous DNA for transfer into the plant cell should be located within the vector between the T-DNA border sequences.

One standard method for T-DNA transfer is the binary system. The binary vector contains the T-DNA borders that are needed for excision and integration, with heterologous DNA inserted between the borders. The essential vir genes of the Ti plasmid act in trans and are supplied on a separate plasmid, called the helper plasmid.

The leaf disk technique can be utilized in conjunction with Agrobacterium-mediated transformation. Briefly, wounded plant cells (such as leaves, roots and stems) are cultured briefly with Agrobacterium cells to initiate transfer of the T-DNA from the Agrobacterium to the plant cell. After several days, the plant tissue is transferred to shoot-inducing media that contains a selective agent. In the case of the BIBAC vector containing the GUS-NPTII plant selective marker, media containing kanamycin would be used. After shoots are formed, the shoots are transferred to a medium that stimulates root formation.

Another method for introduction of the vector or clone into a plant cell is by transformation of the plant cell nucleus, such as by particle bombardment.

A further method for introduction of the vector or clone into a plant cell is by transformation of plant cell protoplasts (stable or transient). Plant protoplasts are enclosed only by a plasma membrane and will therefore take up macromolecules like heterologous DNA. These engineered protoplasts can be capable of regenerating whole plants. Suitable methods for introducing heterologous DNA into plant cell protoplasts include electroporation and PEG transformation.

An additional method for introduction of the vector or clone into a plant cell is by transformation of plant organelles (such as chloroplast or mitochondria), such as by particle bombardment. Although the vector will not replicate in the plant organelles, the heterologous DNA may be incorporated into the genome by recombination.

As used throughout this application, electroporation is a transformation method in which, generally, a high concentration of vector DNA (containing heterologous DNA) is added to a suspension of host cell protoplasts or bacterial cells and the mixture shocked with an electrical field of 200 to 600 V/cm. Following electroporation, transformed cells are identified by growth on appropriate medium containing a selective agent.

As also used throughout this application, particle bombardment (also know as biolistic transformation) of the host cell can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Thus, the vector according to the subject invention can be used to transform a variety of host cells in a variety of ways. Specifically, heterologous DNA encoding the desired gene product can be inserted into the unique restriction endonuclease cleavage site of the BIBAC vector. The vector, containing the heterologous DNA, is used to transform *Escherichia coli*, and/or to transform *Agrobacterium tumefaciens*. *Agrobacterium tumefaciens* is then used to transform plant cells. The introduction of the heterologous DNA into the plant cell allows the production of the gene product encoded by the heterologous DNA when the DNA is expressed in the plant cell.

Alternatively, a desired gene product can be produced in a plant cell by transforming a plant cell directly with the BIBAC vector (having heterologous DNA encoding the gene product inserted into the unique restriction endonuclease cleavage site), such as by biolistic transformation. This method can also introduce the heterologous DNA into the plant cell, allowing the production of the gene product encoded by the heterologous DNA when the DNA is expressed in the plant cell.

With such methods in mind, the vector can be used to clone plant genes by their phenotype. For example, a particular plant is determined to be susceptible to a virus, and a gene encoding for viral resistance is thought to exist. A genomic library is created in the BIBAC vector, and the vector containing the segment of DNA that potentially encodes the viral resistance gene is used to transform the plant. The transformed plant is then exposed to the virus. Lack of the phenotypic traits characteristic of viral infection of the plant indicates that the viral resistance gene has been transferred into the plant by that particular heterologous DNA insert in the BIBAC . vector. Therefore, the sequence encoding the viral resistance gene can be identified, using the BIBAC vector for cloning genes by their phenotype.

As used throughout this application, transformation emcompasses either transient or stable transformation. In transient transformation, heterologous DNA is introduced into a host cell without being incorporated into the DNA of the host cell (incorporation being a stable transformation). In the case of plant transformation, DNA can be transiently introduced into the plant cell, or stably introduced (i.e. incorporated into the plant nuclear genome, chloroplast genome, or mitochondrial genome). In the case of Agrobacterium-mediated plant transformation, heterologous DNA is transiently introduced into the plant cell or stably introduced (i.e. incorporated) into the nuclear genome of the plant. Agrobacterium-mediated plant transformation does not stably incorporate heterologous DNA into the chloroplast or mitochondrial genome of the plant. Transformation as used herein encompasses any of these types of transformation that is available for a particular vector/host combination.

EXAMPLE 1

Construction of the BIBAC

The library features of the BIBAC are based on the bacterial artificial chromosome (BAC) cloning system described by Shizuya et al. (1992). In addition, the vector is a "state of the art" binary vector for Agrobacterium-mediated plant transformation (Hoekema et al. 1983).

Two major groups of components have been incorporated into the BIBAC. The first group includes those functions that are required in its bacterial hosts: *E. coli* and *A. tumefaciens*, and features to help characterize the library. The second group includes those features of the BIBAC which are intended to facilitate Agrobacterium-mediated plant transformation. A map of the BIBAC is shown in FIG. 1.

The backbone of the BIBAC has the minimal region required for F factor replication and maintenance (O'Conner et al. 1989). The λ cosN and P1 loxP sites from pBAC108 are also incorporated into the BIBAC. These sites function as unique restriction sites to anchor one end of the insert and facilitate the analysis of partial digestions with restriction endonuclease(s). The cosN site can be cleaved with the bacteriophage λ terminase (Rackwitz et al. 1985); the loxP site by bacteriophage P1 Cre protein in the presence of the loxP oligonucleotide (Abremski et al. 1983). Restriction maps of the individual clones can be determined by indirect end-labeling and subsequent partial digestion (Rackwitz et al. 1985; Abremski et al. 1983; Kohara et al. 1987).

A marker which provides a positive selection for inserts is incorporated into the BIBAC. This marker is the sacb gene from *Bacillus amyloliquifaciens* (Tang et al. 1990) which encodes the protein levansucrase. Levansucrase was first identified as a 50 kD protein secreted by *Bacillus subtilis* following induction by sucrose. The enzyme catalyzes transfructorylation from sucrose to various receptors (Dedonder 1966). The sacB structural gene of *B. subtilis* was cloned by Gay et al. (1983). Subsequently it was discovered that when 5% sucrose is present in agar media, the production of levansucrase is lethal to *E. coli*, *A. tumefaciens*, and *Rhizobium meliloti* (Gay et al. 1985).

The sacB gene was subcloned from the bacteriophage P1 cloning vector pAd10sacBII (Pierce et al. 1992). (The coding regions of the *B. amyloliquifaciens* and the *B. subtilis* sacb genes show 90% identity at the nucleotide level.) This construct has a BamHI cloning site region and a synthetic *E. coli* promoter upstream of the sacB structural gene. The BamHI cloning site is flanked by T7 and SP6 RNA polymerase promoters which can be used to generate RNA probes for chromosome walking. The Bam HI cloning site is unique to the BIBAC. When a DNA fragment is inserted into the Bam HI site, the sacB gene is inactivated, and the strain is viable when grown on media containing 5% sucrose. The sacB gene was introduced into pBAC108 to generate pCH1. This construct was electroporated into *E. coli* strain DH10B and the resulting strain was tested for sensitivity to high sucrose by plating a dilution series on standard LB media and on LB containing 5% sucrose. Cells plated on LB containing 5% sucrose showed a plating efficiency of less than $10^{-6}$ compared to cells plated on standard LB media. Thus, plating a potential library on 5% sucrose should yield primarily genomic clones.

The BIBAC has the replication origin region from the Ri plasmid of *A. rhizogenes*, the causal agent of hairy root disease. The Ti and Ri plasmids belong to different incompatibility groups and can be maintained stably together in one cell (White and Nester 1980; Constantino et al. 1980). This is important because many *A. tumefaciens strains* used for plant transformation contain a disarmed Ti plasmid as the virulence helper plasmid. The minimal Ri origin region that is incorporated into the BIBAC has been shown to be sufficient for plasmid replication and stable maintenance at 1–2 copies per cell in *A. tumefaciens* (Jouanin et al. 1985). (The "2" copies per cell is included here to cover the presence of the duplicated DNA during cell replication.) The minimal Ri origin was subcloned from pLJbB11 which was characterized by Jouanin et al. (1985). The oriT cassette and the Ri origin were cloned adjacent to each other in pUC19 (Yanisch-Perron et al. 1985) to create pCH9. This was done so that the two components could be transferred to the vector as a single unit.

The BIBAC has an origin of conjugal transfer (ori T) derived from the wide host range plasmid RK2 of the Inc P group. When all other transfer functions are provided in trans by a helper plasmid, the ori T allows for the conjugal transfer of any covalently linked self replicating DNA (Ditta et al. 1980). The RK2 oriT of the BIBAC is subcloned from a DNA cassette in pNHKan-oriT constructed by Hengen and Iyer (1992). The BIBAC can be transferred to *A. tumefaciens* by conjugation. The RK2 ori T has been used to effect the conjugal transfer of the chromosomes of *E. coli* and *Rhizobium meliloti* (Yakobson and Guiney 1984). Therefore conjugal transfer of high molecular weight DNA from *E. coli* to *A. tumefaciens* is possible. Alternatively, BIBAC clones can be introduced into Agrobacterium by electroporation. Mozo and Hooykaas (1991) reported that plasmids as large as 250 kb can be introduced into *A. tumefaciens* by electroporation.

The features that are incorporated into the BIBAC to facilitate use of the vector in plant transformation are: *A. tumefaciens* T-DNA borders, and plant selectable markers. There were two criteria for choosing the borders of the BIBAC: 1) to make plant transformation as efficient as possible; and 2) to make the vector compatible with *A. tumefaciens* disarmed Ti plasmids which carry octopine-type, nopaline-type, or supervirulence-type virulence genes.

Figure 2:
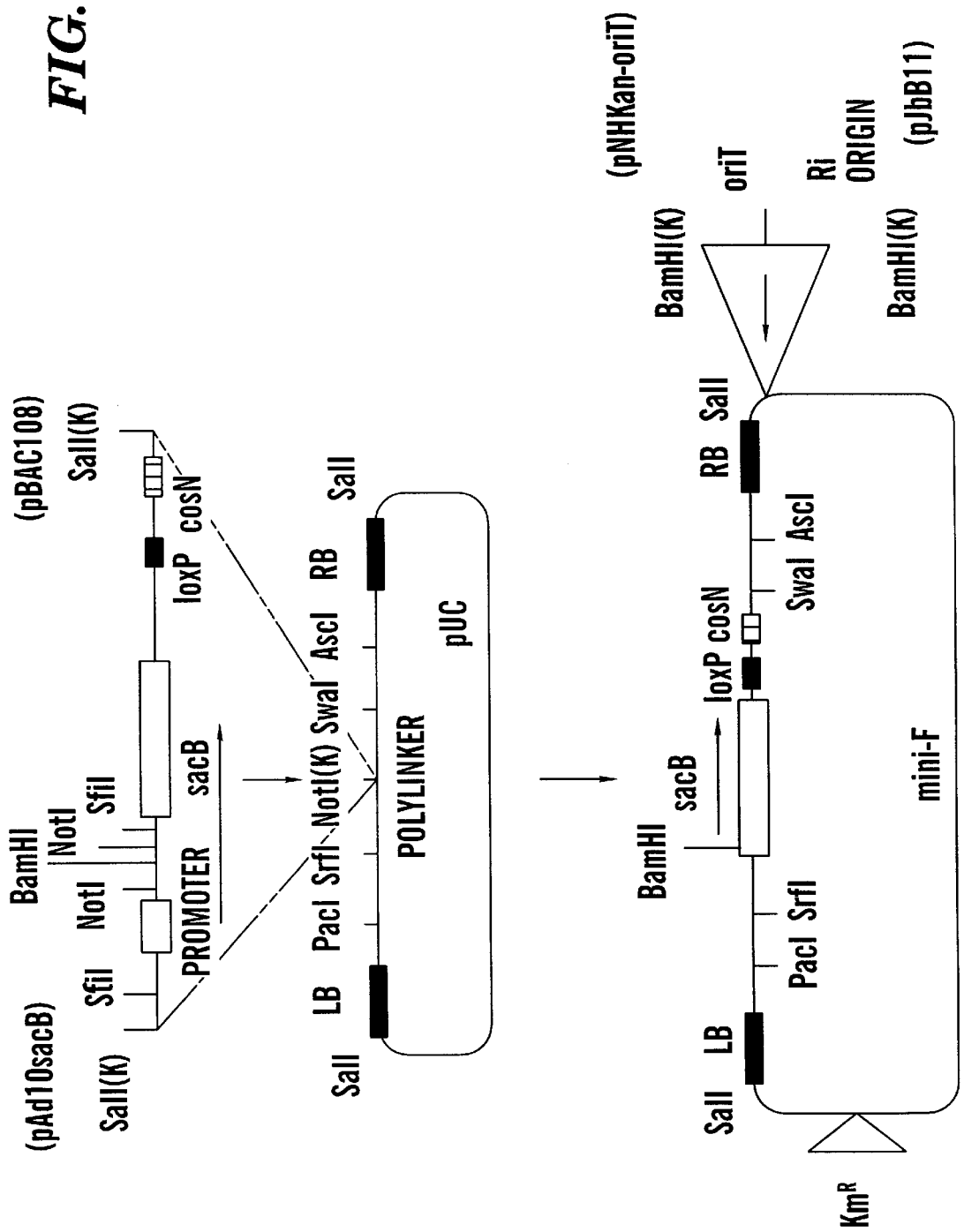
FIG. 2 shows the strategy for construction of the BIBAC vector.

FIG. 2 illustrates the construction of the BIBAC. The right and left border sequences of the BIBAC are derived from the TL-DNA of the octopine plasmid pTiA6. The right border "overdrive" sequences are present (Peralta et al. 1986; van Haaren et al. 1987). The borders in the BIBAC were generated by Pfu. polymerase PCR using primers which hybridize to cosmid pVK232 (Knauf and Nester 1982). The plasmid pVK232 contains the entire TL-DNA of TiA6 (de Vos et al. 1981; Barker et al. 1983; Gielen et al. 1984). A synthetic polylinker connects the border sequences, and is designed to provide unique cloning sites adjacent to the right and left border sequences to facilitate the introduction of plant selectable markers. These are designated MSR (marker site right) and MSL (marker site left) in FIG. 1. The PCR generated borders and the polylinker were initially cloned into pUC19.

As a result, the right and left borders and the polylinker are carried on a Sal I fragment in pCH7. This was done to facilitate the subsequent cloning of this fragment into the Sal I site of mini-F pMBO131.

The sacB gene was cloned into pCH7 by transforming a pcnb strain of *E. coli* and incubation of the transformants at 30° C. If a pUC type plasmid is propagated at 30° C., then its copy number is reduced from 80 to 20 copies per cell (Lin-Chao et al. 1992). The pcnb (plasmid copy number) mutation reduces the copy number of ColE1 type plasmids from about 20 copies per cell, to about 1 copy per cell (Lopilato et al. 1986). These conditions were used to obtain the desired construct, pCH10. When the Sal I fragment from pCH10 was introduced into the mini-F to make pCH13, positive clones were easily identified by screening for the sacb marker. The oriT/Ri origin fragment was then introduced into a unique Hpa I site which is 35 nucleotides from the Sal I edge of the mini-F to make pCH16. Preliminary experiments indicated that chloramphenicol is not a useful marker for some strains of Agrobacterium, so a kanamycin resistance gene cassette (Smith and Crouse 1989) was cloned into the Pvu II site of the chloramphenicol gene of the mini-F to complete the backbone of the BIBAC.

Transfer of the T-DNA is initiated at the right border and proceeds toward the left border, so the transfer of the plant selectable marker located near the left border is indicative of the transfer of the entire T-DNA. Therefore it is critical to have a plant selectable marker at the MSL. If desired, a second plant selectable marker can be introduced at the MSR. For some applications it might be useful to introduce a Ds element at the MSR. The GUS-NPTII construct (Datla et al. 1991) is a bifunctional fusion peptide between *E. coli* β-glucuronidase (GUS) and neomycin phosphotransferase II (NPTII). When this construct is expressed in the plant, the transformed plant is resistant to neomycin and can be assayed for expression of the GUS gene (Jefferson et al. 1987). This GUS-NPTII construct is carried on an Eco RI-Hin dIII fragment. The fragment was treated with Klenow and ligated into the Srf I site at the MSL site to create BIBAC1.

Several BIBACs have been constructed that carry other plant selectable markers. BIBAC2 carries the BAR-GUS construct at MSL. The BAR-GUS construct (Fromm et al. 1990) is a bifunctional fusion peptide between the gene for phosphinothricin acetyltransferase (BAR) which imparts resistance to the herbicide phosphinothricin, and the GUS gene. The GUS-NPTII and BAR-GUS constructs are driven by a strong double CaMV 35S promoter (Kay et al. 1987) and termination sequences derived from the nopaline synthase gene. In addition an AMV (alfalfa mosaic virus) enhancer is present in the GUS-NPTII construct.

If two plant selectable markers are desired in a BIBAC vector, the promoters and transcription termination sequences of the two constructs should be nonhomologous. This is to prevent any sequence redundancy within the vector which might reduce its stability. This caveat should also be considered in the event that someone wants to incorporate some other plant selectable marker. In addition, any pairs of plant selectable markers should be oriented in the BIBAC so that they are not convergently transcribed, as this configuration may impair transgene expression (Jones et al. 1992). In the BAC, where the markers may be separated by 200 kb of plant genomic DNA, this is not likely to be a problem. However, control experiments using the vector alone might be compromised.

BIBAC3 carries the HYG construct at the MSL in addition to the GUS-NPTII construct at the MSR. The hygromycin phosphotransferase (HYG) construct provides resistance to hygromycin (Becker, et al. 1992). The HYG construct has a nopaline synthase promoter, and terminator sequences from pAg7. Any other plant selectable marker can be readily introduced at one of the unique polylinker sites. Of course, the plant selectable marker must not have a Bam HI site, so that the library cloning site will still be unique.

EXAMPLE 2

Testing of the BIBAC Vector

BIBAC1 has been used for initial tests. A physical map of BIBAC1 has been established, and the vector alone (without any DNA insert) functions as expected. It replicates in *E.coli* and *A. tumefaciens* and is capable of transferring its T-DNA to tobacco. Tomato and yeast heterologous DNA have been inserted into the BamHI site of the BIBAC vector. Each resulting clone (which includes the vector and the heterologous DNA) was then introduced into *Escherichia coli* strain DH10B by electroporation. The *E. coli* strain DH10B has been widely used for construction of genomic libraries, and stability is not expected to be a problem for the majority of BIBAC clones. The DH10B strain contains recA1 which increases the stability of the inserts, as well as mcrA, mcrB, mcrc, and mrr, which in combination prevent the restriction of DNA which contains methylated cytosine and adenine residues. That is, it should not be a problem to clone even heavily methylated plant genomic DNA using this strain.

A triparental mating was then performed with the resulting *Escherichia coli*, an *Escherichia coli* containing a helper plasmid pRK2073 (which carries resistance to spectinomycin (Leong et al. 1982)), and *Agrobacterium tumefaciens*. After transfer of the vector to *Agrobacterium tumefaciens*, tobacco plants were transformed using the method described in Example 3 below.

Transgenic plants have been obtained with BIBAC1 in Agrobacterium strains EHA105 (Hood et al. 1993) which carries a disarmed supervirulent-type Ti plasmid, LBA4404 (Ooms et al. 1982) which carries an octopine-type disarmed Ti plasmid, GV3101 (Koncz and Schell 1986) which carries pMP90, a nopaline-type disarmed Ti plasmid, and a recA- strain of *A. tumefaciens*, UIA143 (Farrand et al. 1989), transformed with pMP90.

Of the first nine BIBAC1 transgenic plants screened by PCR for the presence of a fragment unique to the BIBAC1 T-DNA, all nine tested positive. The PCR method might also detect *A. tumefaciens* bacteria that have remained associated with the leaf tissue, as well as detecting stably transformed DNA. To confirm the PCR results, the genomic DNA from these plants is subjected to Southern analysis using the BIBAC1 T-DNA as a probe.

EXAMPLE 3

Transformation of Tobacco Plants

Agrobacterium strains were introduced into plants by Agrobacterium-mediated transformation of tobacco leaf strips. Transformed plants were identified by selecting for kanamycin resistance. Putative transgenic plants were screened by PCR (Saiki 1988).

The method used for Agrobacterium-mediated transformation is a modification of Horsch et al. (1985) as follows.

Agrobacterium-mediated leaf explant transformation

Day 1

From young, healthy plants (such as *Nicotiana tabacum* (tobacco) Petit Havana) pick young leaves. A good rough estimate for proper amount is to obtain enough leaf surface area to cover the bottom of 1 to 2 standard size petri dishes.

To a jar containing approximately 400 ml sterile distilled water, add 40 ml of bleach and 4 ml of 5% SDS to give approximately 0.05% SDS. Add a stir bar and all of the leaves to the jar. Cover the jar with a lid. Stir for 20 minutes, adjusting speed so that leaves are not damaged.

In the sterile air hood, rinse leaves by transferring them into a jar containing 400 ml sterile distilled water. Use sterile forceps to transfer leaves. Swirl leaves by shaking jar gently. After 5 minutes, transfer to a second jar of sterile distilled water. After 5 minutes, transfer to a third jar. The leaves can remain in this final rinse until you are ready to work in the sterile air hood. Keep the jar covered with a lid.

Do the following in the sterile air hood. To prepare strips, transfer leaves to a sterile petri dish, placing them upside down in the dish (i.e. lower epidermis up). While holding onto the midrib with sterile forceps, use a sterile scalpel to slice each leaf perpendicular to the midrib into numerous thin strips. Strips should be about 5 mm in width.

Alternatively, plants grown from surface sterilized seed under sterile conditions can be used directly.

Place 5 strips right side up on each of two regeneration plates. These will be controls to check whether uninoculated leaves will regenerate on the medium without antibiotics. Note 100×20 mm plates are used with explants to allow room for plant growth. 100×26 mm plates could also be used. (Standard bacterial plates are 100×15 mm).

Take three regeneration plates to use for pre-culture of explants. Place about 15 strips upside down on each plate. More material than will be needed is precultured, since some of it may become contaminated or damaged.

NOTE: It doesn't really matter whether you pre-culture the leaf material upside down or right side up. The protocol specifies upside down because the underside is usually more vulnerable to damage. After preculture, when it is time to inoculate, it is easy to observe leaf strips or disks with damaged lower epidermis. Such leaf explants are discarded.

Seal plates of explants prepared as above with parafilmn and place in a lighted incubator at 25–28° C. (some investigators pre-culture in the dark).

NEXT DAY (Day 2)

Take a single-streaked LB kan plate containing electroporated Agrobacterium. From two single colonies, start a 5 ml overnight culture in LB medium containing 50 ug/ml kanamycin. Repeat to make a duplicate tube. Incubate with shaking at 30° C.

NEXT DAY (Day 3)

Place 5 leaf strips right side up on each of two plates of regeneration medium containing carbenicillin plus kanamycin or timentin plus kanamycin. Thee will be controls to test whether any uninoculated tissue can grow and/or form shoots on selective medium.

Some species' leaf explants produce more shoots when placed right side up; hence the instructions to place the strips on the regeneration plates right side up.

Put parafilm around the dishes.

Dilute the overnight culture of Agrobacterium 1:10 by mixing 2 ml with 18 ml of MSO medium. Pour the dilution into a sterile petri dish.

Discard leaf strips which are obviously damaged or have not swollen from the pre-culture plates. Place the healthy strips into the diluted bacterial culture and swirl the dish gently for no more than 5 seconds so that the cut edges become wet.

WARNING—Do not leave the leaf tissue in the culture any longer than is needed to wet all the wounded edges with the inoculum. Saturating the tissue with bacteria may result in incurable infection.

Remove the tissue from the bacterial culture, and place it on a sterile Whatman no. 1 filter paper to blot off some of the excess bacterial culture. Then place 10 strips upside down, on two regeneration plates (without antibiotics).

Put parafilm around the dishes and incubate the dishes lid side up.

(Some laboratories find it helpful to use a nurse cell culture, especially with species of plants that are difficult to regenerate. They add 1 to 1.5 ml of a rapidly growing liquid plant suspension culture to a regeneration plate and completely cover this with a sterile Whatman #1 filter paper. The filter paper prevents contamination of the explants with the cells. Then they place leaf strips on top of the filter paper. Tobacco suspension culture cells are often used because these cells are grown in a medium which does not contain 2,4-D. 2,4-D would inhibit plant regeneration if used in the nurse culture.)

THREE DAYS LATER

Transfer the leaf strips and/or disks to regeneration plates containing 500 ug/ml carbenicillin or 100 ug/ml tementin to kill the bacteria, and 300 ug/ml kanamycin to select for transformed cells which express kanamycin resistance. Place the leaf tissue right side up on the medium.

LATER STILL . . .

Shoots will begin to form on the leaf tissue in 2 to 3 weeks in a lighted growth chamber at 25–28° C. After 2 weeks transfer explants to fresh regeneration plates with carbenicillin (or tementin) and kanamycin.

Continue to examine the dishes frequently. When callus knobs form, transfer them (without the leaf tissue) to fresh regeneration plates with carbenicillin and kanamycin.

After about 1 to 2 more weeks shoots will form on the callus. When the shoots are big enough so that you can cut them off above the callus, do this and transfer the shoots to rooting medium with carbenicillin plus kanamycin or tementin plus kanamycin. It is important to avoid callus contamination of the shoots because the callus is likely to still contain some Agrobacterium. Reducing or omitting kanamycin sometimes helps to speed up the rooting process.

Continue to observe the dishes. If any growth of Agrobacterium is seen, immediately transfer the shoots to fresh rooting medium with carbenicillin or tementin plus kanamycin. If the Agrobacterium growth is limited to a small number of shoots, transfer only those without visible Agrobacterium outgrowth to new medium, and discard the old dish.

After roots have formed, transfer the little plants to Magenta boxes containing rooting medium without antibiotics.

When plants have 4 to 5 leaves and roots that are 3 to 4 cm long, they can be potted in soil. When potting, remove the agar from the roots. Enclose each newly potted plant in a plastic bag that is closed at the top with a twist tie. Gradually (over a period of about 2 weeks) open the bag or cut it to make a larger and larger opening. Then remove the bag.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Abremski, K. et al. (1983). Studies of the properties of P1 site-specific recombination: evidence for topolgically unlinked products following recombination. Cell 32, 1310–1311.

Anderson, C. (1993). Genome shortcut leads to problems. Science 259, 1684–1687.

Barker, R. F. et al. (1983). Nucleotide sequence of the T-DNA region from the *Agrobacterium tumefaciens* octopine Ti plasmid pTi15955. Plant Mol. Biol. 2, 335–350.

Becker, D. et al. (1992). New plant binary vectors with selectable markers located proximal to the left T-DNA border. Plant Mol. Biol. 20, 1195–1197.

Bennett, M. D., and Smith, J. B. (1976). Nuclear DNA amounts in angiosperms. Phil. Trans. Roy. Soc. Lond. 274, 224–274.

Bent, A. F. et al. (1994). RPS2 of *Arabidopsis thaliana*: A leucine-rich repeat class of plant disease resistance gene. Science 265, 1856–1860.

Burke, D. et al. (1987). Cloning of large segments of exogenous DNA into yeast by means of artificial chromosome vectors. Science 236, 806–812.

Constantino, P. et al. (1980). Tumor formation and rhizogenicity of *Agrobacterium rhizogenes* carrying Ti plasmids. Gene 11, 79–87.

Datla, R. S. S. et al. (1991). A bifunctional fusion between β-glucuronidase and neomycin phosphotransferase: a broad-spectrum marker enzyme for plants. Gene 101, 239–246.

Dedonder, R. (1966). Levansucrase from *Bacillus subtilis*. Meth. Enzymol. 8, 500–505.

de Vos, G. et al. (1981). Restriction endonuclease mapping of the octopine tumor inducing plasmid pTiAch5 of *Agrobacterium tumefaciens*. Plasmid 6, 249–253.

Ditta, G. et al. (1980). Broad host range DNA cloning system for gram-negative bacteria: Construction of a gene bank of *Rhizobium meliloti*. Proc. Natl. Acad. Sci. USA. 77, 7347–7351.

Farrand, S. K. et al. (1989). Construction of an *Agrobacterium tumefaciens* C58 recA mutant. J. Bact. 171, 5314–5321.

Fromm, M. E. et al. (1990). Inheritance and expression of chimeric genes in the progeny of transgenic maize plants. Bio/Tech. 8, 833–839.

Gay, P. et al. (1983). Cloning structural gene sacB, which codes for exoenzyme levansucrase of *Bacillus subtilis*: Expression of the gene in *Escherichia coli*. J. Bact. 153, 1424–1431.

Gay, P. et al. (1985). Positive selection procedure for entrapment of insertion sequence elements in gram-negative bacteria. J. Bact. 164, 918–921.

Gielen, J. et al. (1984). The complete nucleotide sequence of the TL-DNA of the *Agrobacerium tumefaciens* plasmid pTiAch5. EMBO J. 3, 835–846.

Hengen, P. N., and Iyer, V. N. (1992). DNA cassettes containing the origin of transfer (oriT) of two broad-host-range transfer systems. BioTech. 13, 56–62.

Hiei, Y. et al. (1994). Efficient transformation of rice (Oryza sativa L.) mediated by Agrobacterium and sequence analysis of the boundaries of the T-DNA. Plant J. 6, 271–282.

Hoekema, A. et al. (1983). A binary plant vector strategy based on separation of vir- and T-region of the *Agrobacterium tumefaciens* Ti-plasmid. Nature 303, 179–180.

Hood, E. E. et al. (1993). New Agrobacterium helper plasmids for gene transfer to plants. Transgenic Research 2, 208–218.

Horsch, R. B. et al. (1985). A simple and general method for transferring genes into plants. Science 227, 1229–1231.

Jefferson, R. A. et al. (1987). GUS fusions: β-glucuronidase as a sensitive and versatile gene fusion marker in higher plants. EMBO J. 6, 3901–3907.

Jones, J. D. G. et al. (1992). Effective vectors for transformation, expression of heterologous genes, and assaying transposon excision in transgenic plants. Transgenic Research 1, 285–297.

Jones, D. A. et al. (1994). Isolation of the tomato Cf-9 gene for resistance to *Cladisporium fulvum* by transposon tagging. Science 266, 789–794.

Jouanin, L. et al. (1985). Localization and restriction maps of the replication origin regions of the plasmids of *Agrobacterium rhizogenes* strain A4. Mol. Gen. Genet. 201, 370–374.

Kado, C. I. (1991). Molecular mechanisms of crown gall tumorigenesis. Critical Reviews in Plant Sciences 10, 1–32.

Kay, R. et al. (1987). Duplication of CaMV 35S promoter sequences creates a strong enhancer for plant genes. Science 236, 1299–1302.

Knauf, V. C., and Nester, E. W. (1982). Wide host range cloning vectors: a cosmid clone bank of an Agrobacterium Ti plasmid. Plasmid 8, 45–54.

Kohara, Y. et al. (1987). The physical map of the whole *E. coli* chromosome: application of a new strategy for rapid analysis and sorting of a large genomic library. Cell 50, 495–508.

Koncz, C., and Schell, J. (1986). The promoter of TL-DNA gene 5 controls the tissue-specific expression of chimaeric genes carried by a novel type of Agrobacterium binary vector. Mol. Gen. Genet. 204, 383–396.

Leong, S. A. et al. (1982). Heme biosynthesis in Rhizobium. Identification of a cloned gene coding for S-aminolevulinic acid synthetase from *Rhizobium meliloti*. J. Biol. Chem. 257, 8724–8730.

Lin-Chao, S. et al. (1992). High copy number of the pUC plasmid results from a Rom/Rop-suppressible point mutation in RNAII. Molec. Microbiol. 6, 3385–3393.

Lopilato, J. et al. (1986). Mutations in a new chromosomal gene of *Escherichia coli* K-12, pcnB, reduce plasmid copy number of pBR322 and its derivatives. Mol. Gen. Genet. 205, 285–290.

Low, K. B. (1972). *Escherichia coli* K-12 F-prime factors old and new. Bacteriol. Rev. 36, 587–607.

Ma, H. et al. (1992). Vectors for plant transformation and cosmid libraries. Gene 117, 161–167.

Martin, G. B. et al. (1991). Rapid identification of markers linked to a Pseudomonas resistance gene in tomato by using random primers and near-isogenic lines. Proc. Natl. Acad. Sci. USA. 88, 2336–2340.

Martin, G. B. et al. (1992). Construction of a yeast artificial chromosome library of tomato and identification of cloned segments linked to two disease resistance loci. Mol. Gen. Genet. 233, 25–32.

Martin, G. B. et al. (1993). Map-based cloning of a protein kinase gene conferring disease resistance in tomato. Science 262, 1432–1436.

Michelmore, R. W. et al. (1991). Identification of markers linked to disease-resistance genes by bulked segregant analysis: A rapid method to detect markers in specific genomic regions by using segregating populations. Proc. Natl. Acad. Sci. USA. 88, 9828–9832.

Miranda, A. et al. (1992). *Agrobacterium tumefaciens* transfers- extremely long T-DNAs by a unidirectional mechanism. J. Bact. 174, 2288–2297.

Mozo, T., and Hooykaas, P. J. J. (1991). Electroporation of megaplasmid into Agrobacterium. Plant Mol. Biol. 16, 917–918.

O'Conner, M. et al. (1989). Construction of large DNA segments in *Escherichia coli*. Science 244, 1307–1312.

Ooms, G. et al. (1982). Octopine Ti-plasmid deletion mutants of *Agrobacterium tumefaciens* with emphasis on the right side of the T-region. Plasmid 7, 15–29.

Peralta, E. G., and Ream, L. W. (1985). T-DNA border sequence required for crown gall tumorigenesis. Proc. Natl. Acad. Sci. USA. 82, 5112–5116.

Peralta, E. G. et al. (1986). Overdrive, a T-DNA transmission enhancer on the *A. tumefaciens* tumor-inducing plasmid. EMBO J. 5, 1137–1142.

Pierce, J. C. et al. (1992). A positive selection vector for cloning high molecular weight DNA by the bacteriophage P1 system: Improved cloning efficacy. Proc. Natl. Acad. Sci. USA. 89, 2056–2060.

Rackwitz, H. R. et al. (1985). Analysis of cosmids using linearization by phage lambda terminase. Gene 40, 259–266.

Saiki, R. K. (1988). Optimization of the polymerase chain reaction. In: *Current Communications in Molecular Biology: Polymerase Chain Reaction*, H. A. Erlich et al., eds. (New York: Cold Spring Harbor Laboratory Press), pp. 25–30.

Shizuya, H. et al. (1992). Cloning and stable maintenance of 300-kilobase-pair fragments of human DNA in *Escherichia coli* using an F-factor-based vector. Proc. Natl. Acad. Sci. USA. 89, 8794–8797.

Smith, M. L., and Crouse, G. F. (1989). Construction of linker-scanning mutations using a kanamycin-resistance cassette with multiple symmetric restriction sites. Gene 84, 159–164.

Southern, E. M. (1975). Detection of specific sequences among DNA fragments separated by gel electrophoresis. J. Mol. Biol. 98, 503–517.

Tang, L. B. et al. (1990). Isolation and characterization of levansucrase-encoding gene from *Bacillus amyloliquefaciens*. Gene 96, 89–93.

van Haaren, M. J. J. et al. (1987). Overdrive is a T-region transfer enhancer which stimulates T-strand production in *A. tumefaciens*. Nucleic Acids Res. 15, 8983–8997.

van Wordragen, M. F., and Dons, H. J. M. (1992). *Agrobacterium tumefaciens*-mediated transformation of recalcitrant crops. Plant Mol. Biol. Rep. 10, 12–36.

Wang, G., and Ronald, P. C. (1994) Construction of a bacterial artificial chromosome (BAC) library for physical mapping and cloning of a bacterial blight resistance gene Xa-21. Abstract P214 from the "Second International Conference on the Plant Genome", San Diego, Calif., January 1994.

White, F. F., and Nester, E. W. (1980). Relationship of plasmids responsible for hairy root and crown gall tumorigenicity. J. Bact. 144, 710–720.

Whitham, S. et al. (1994). The product of the tobacco mosaic virus resistance gene N: Similarity to toll and the interleukin-1 receptor. Cell. 78, 1101–1115.

Williams, J. G. K. et al. (1990). DNA polymorphisms amplified by arbitrary primers are useful as genetic markers. Nucleic Acids Res. 18, 6531–6535.

Woo, S.-S. et al. Construction and characterization of a bacterial artificial chromosome library for Sorghum bicolor. Abstract P223 from the "Second International Conference on the Plant Genome", San Diego, Calif., January 1994.

Yakobson, E. A., and Guiney, D. G. J. (1984). Conjugal transfer of bacterial chromosomes mediated by the RK2 plasmid transfer origin cloned into transposon Tn5. J. Bact. 160, 451–453.

Zabeau, M., and Vos, P. (1992): Selective restriction fragment amplification: a general method for DNA fingerprinting. (Assigned to Keygene N.V.) European Patent Application No. EP 91402542, published Sep. 24, 1991. Netherlands Patent No. 0 534 858 A1, issued Mar. 31, 1993.

Zambryski, P. (1988). Basic processes underlying Agrobacterium-mediated DNA transfer to plant cells. Ann. Rev. Genet. 22, 1–30.

What is claimed is:

1. A method of making a transgenic plant transformed with a vector comprising:

providing a vector comprising:

a backbone which includes a first origin of replication capable of maintaining heterologous DNA as a single copy in an *Escherichia coli* host cell, and which further includes a second origin of replication capable of maintaining heterologous DNA as a single copy in an *Agrobacterium tumefaciens* host cell, a unique restriction endonuclease cleavage site for insertion of heterologous DNA, a heterologous DNA encoding a gene product inserted into the unique restriction site, and left and right Agrobacterium T-DNA border sequences flanking said unique restriction endonuclease cleavage site, said left and right T-DNA border sequences allowing introduction of heterologous DNA located between said left and right T-DNA border sequences into a plant cell; introducing said vector into plant cells; and propagating plants from said plant cells.

2. The method of making a transgenic plant of claim 1 wherein said introducing said vector into plant cells comprises:

transforming an *Escherichia coli* host cell with the resulting vector to introduce said heterologous DNA into said *Escherichia coli* host cell;

transforming an *Agrobacterium tumefaciens* host cell with a vector DNA isolated from the resulting *Escherichia coli* host cell to introduce said heterologous DNA into said *Agrobacterium tumefaciens* host cell; and transforming a plant cell with the resulting *Agrobacterium tumefaciens* cell to introduce said heterologous DNA into said plant cell.

3. The method of making a transgenic plant of claim 1 further comprising:

expressing said heterologous DNA in said plant cell to produce the gene product encoded by said heterologous DNA in said plant cell.

4. The method of making a transgenic plant of claim 1, wherein the vector further comprises a selection marker for introduction of said heterologous DNA into a plant cell, said selection marker located between said left and right T-DNA border sequences.

5. The method of making a transgenic plant of claim 4, wherein said selection marker is located adjacent to said left T-DNA border sequence.

6. The method of making a transgenic plant of claim 4, wherein said selection marker comprises a kanamycin resistance gene.

7. The method of making a transgenic plant of claim 6, wherein said kanamycin resistance gene comprises a GUS-NPTII gene.

8. The method of making a transgenic plant of claim 4, wherein said selection marker comprises a hygromycin resistance gene.

9. A transgenic plant produced by the method according to claim 1.

10. A seed isolated from the transgenic plant of claim 9.

11. The transgenic plant of claim 9, wherein the insert of heterologous DNA is longer than 46 kilobases.

12. The transgenic plant of claim 9 further comprising a selection marker for introduction of said heterologous DNA into a plant cell, said selection marker located between said left and right T-DNA border sequences.

13. The transgenic plant of claim 12, wherein said selection marker is located adjacent to said left T-DNA border sequence.

14. The transgenic plant of claim 12, wherein said selection marker comprises a kanamycin resistance gene.

15. The transgenic plant of claim 14, wherein said kanamycin resistance gene comprises a GUS-NPTII gene.

16. The transgenic plant of claim 12, wherein said selection marker comprises a hygromycin resistance gene.

17. A method of introducing heterologous DNA into a plant cell comprising:

providing a vector comprising:

a backbone which includes a first origin of replication capable of maintaining heterologous DNA as a single copy in an *Escherichia coli* host cell, and which further includes a second origin of replication capable of maintaining heterologous DNA as a single copy in an *Agrobacterium tumefaciens* host cell, a unique restriction endonuclease cleavage site for insertion of heterologous DNA, a heterologous DNA encoding a gene product inserted into the unique restriction endonuclease cleavage site, and left and right Agrobacterium T-DNA border sequences flanking said unique restriction endonuclease cleavage site, said left and right T-DNA border sequences allowing introduction of heterologous DNA located between said left and right T-DNA border sequences into a plant cell; and introducing said vector into plant cells.

18. The method of introducing heterologous DNA into a plant cell according to claim 17, wherein said introducing said vector into plant cells comprises:

transforming an *Escherichia coli* host cell with the resulting vector to introduce said heterologous DNA into said *Escherichia coli* host cell;

transforming an *Agrobacterium tumefaciens* host cell with a vector DNA isolated from the resulting *Escherichia coli* host cell to introduce said heterologous DNA into said *Agrobacterium tumefaciens* host cell; and transforming a plant cell with the resulting *Agrobacterium tumefaciens* cell to introduce said heterologous DNA into said plant cell.

* * * * *